(12) United States Patent
Park et al.

(10) Patent No.: US 8,376,964 B2
(45) Date of Patent: Feb. 19, 2013

(54) APPARATUS FOR ANALYZING A SLEEP STRUCTURE ACCORDING TO NON-CONSTRAINED WEIGHT DETECTION

(75) Inventors: Kwang-Suk Park, Seoul (KR); Do-Un Jeong, Seoul (KR); Jin-Woo Seo, Seoul (KR); Hong-Bum Shin, Seoul (KR); Jong-Min Choi, Seoul (KR); Byung Hun Choi, Junju-si (KR); Jong Hee Han, Gumi-si (KR)

(73) Assignee: Seoul National University Industry Foundation, Seoul (KR)

( * ) Notice: Subject to any disclaimer, the term of this patent is extended or adjusted under 35 U.S.C. 154(b) by 854 days.

(21) Appl. No.: 11/631,908

(22) PCT Filed: Oct. 27, 2005

(86) PCT No.: PCT/KR2005/003597
§ 371 (c)(1),
(2), (4) Date: Jan. 5, 2007

(87) PCT Pub. No.: WO2006/088280
PCT Pub. Date: Aug. 24, 2006

(65) Prior Publication Data
US 2007/0191742 A1    Aug. 16, 2007

(30) Foreign Application Priority Data
Feb. 17, 2005    (KR) .................. 10-2005-0013316

(51) Int. Cl.
*A61B 5/103* (2006.01)
(52) U.S. Cl. .................. 600/587; 600/595
(58) Field of Classification Search .......... 600/300, 600/587
See application file for complete search history.

(56) References Cited

U.S. PATENT DOCUMENTS

| | | | |
|---|---|---|---|
| 5,276,432 A * | 1/1994 | Travis | 340/573.4 |
| 5,479,939 A * | 1/1996 | Ogino | 600/595 |
| 6,280,392 B1 * | 8/2001 | Yoshimi et al. | 600/534 |
| 2003/0111275 A1* | 6/2003 | Sternberg | 177/144 |
| 2005/0085738 A1* | 4/2005 | Stahmann et al. | 600/529 |
| 2005/0124864 A1* | 6/2005 | Mack et al. | 600/300 |
| 2006/0129047 A1* | 6/2006 | Ruotoistenmaki | 600/483 |
| 2006/0241510 A1* | 10/2006 | Halperin et al. | 600/534 |

OTHER PUBLICATIONS

Suppappola, S., and Sun, Y., Nonlinear Transforms of ECG Signals for Digital QRS Detection: A Quantitative Analysis, IEEE Tran. Biomed. Eng. 1994. 41(4): pp. 397-400.

* cited by examiner

*Primary Examiner* — Max Hindenburg
*Assistant Examiner* — Renee Danega
(74) *Attorney, Agent, or Firm* — Bachman & LaPointe, P.C.

(57) ABSTRACT

The present invention relates to an apparatus for analyzing a sleep structure according to non-restrictive weight detection. The apparatus includes load cells one installed in the predetermined locations of a bed and configured to detect the weight of a target person; low-pass filters for outputting low-pass filtered signals that belong to the outputs of the load cells; high-pass filters for outputting high-pass filtered signals that belong to the outputs of the load cells; a multiplexer for selecting any one from among the outputs of the low-pass filters and the high-pass filters; a controller configured to detect information about the target person's sleep from the low-pass filtered signals and the high-pass filtered signals, which belong to the outputs of the high-pass filters and the low-pass filters, respectively, and are input through the multiplexer, and determine the target person's sleeping pattern; and a display unit for displaying determination results of the controller.

11 Claims, 16 Drawing Sheets

FIG.5

| Target person | Variation in center of gravity | | Variation in center of gravity when there is movement | |
|---|---|---|---|---|
| | Total variation | Variation per second | Total variation | Variation per second |
| 1 | 3512.2m | 130mm/sec | 76.5m | 143mm/sec |
| 2 | 3211.4m | 148mm/sec | 112.1m | 157mm/sec |
| 3 | 3382.6m | 144mm/sec | 143.7m | 156mm/sec |
| mean | 3368.7m | 141mm/sec | 110.8m | 152mm/sec |

FIG.9

| Stage | Intensity (kgf/sec) | | Duration (sec/epoch) | | Frequency (n/epoch) |
|---|---|---|---|---|---|
| | move | not move | move | not move | |
| REM | 12.04 | 13.69 | 0.70 | 29.3 | 0.159 |
| Wake | 122.3 | 15.15 | 5.68 | 24.3 | 0.752 |
| 1 | 10.09 | 13.25 | 0.46 | 29.54 | 0.074 |
| 2 | 3.3 | 12.90 | 0.15 | 29.85 | 0.027 |
| 3 | 1.61 | 12.21 | 0.12 | 29.89 | 0.02 |
| 4 | 0 | 0 | 0 | 0 | 0 |

FIG. 13

| | $n(ECG)$ | $n(BCG)$ | $n(ECG_{non})$ | $n(BCG_{consistent})$ | $\dfrac{n(BCG_{consistent})}{n(ECG_{non})}$ | $t_{delay}$ |
|---|---|---|---|---|---|---|
| Target person | 22,546 | 21,099 | 21,090 | 19,700 | 0.934 | 0.403 | ch2 (left upper)

ch1 (right upper)

ch4 (left lower)

ch3 (right lower)

ch2 (left upper)

ch1 (right upper)

ch4 (left lower)

ch3 (right lower)

1

APPARATUS FOR ANALYZING A SLEEP STRUCTURE ACCORDING TO NON-CONSTRAINED WEIGHT DETECTION

TECHNICAL FIELD

The present invention relates, in general, to an apparatus for analyzing a sleep structure according to non-restrictive weight detection and, more particularly, to an apparatus for analyzing a sleep structure according to non-restrictive weight detection, which allows weight detection devices to be installed in equipment, such as a bed that can be slept in, and measures variation in weight that depends on the movement or tossing and turning of a sleeping person, so that information about movement and location during sleep can be analyzed and the characteristics of heartbeat and variation in position during sleep can be detected.

BACKGROUND ART

Generally, in sleep medical science, the sleeping stages of a sleeping person are divided into wakefulness/stages 1~4Rapid Eye Movement (REM) sleep, and the quality of sleep of the sleeping person is evaluated through the analysis of the sleeping stages.

Currently, for technology for analyzing the sleeping stages of a sleeping person, [1] the analysis of sleeping stages using the frequency analysis of an electroencephalogram, [2] the analysis of sleeping stages using Heart Rate Variability (HRV), [3] the analysis of sleeping stages using oxygen saturation, and [4] the analysis of sleeping stages using an actigraph and an accelerometer are mainly used. Of the above-described methods, methods used for easily analyzing the sleeping stages at low cost are the methods [3] and [4].

[1] The method using an electroencephalogram considerably inconveniences a sleeping person because the sleeping person must sleep with electrodes attached to his or her head, and uses a high-priced brain wave amplifier, so that it is used only for special examination in a hospital.

[2] The method for measuring HRV also inconveniences a sleeping person in the case where electrodes are used. Furthermore, there is technology for detecting variation in heartbeat through non-restrictive electrocardiogram measurement using conductive fiber. However, in this technology, the skin of the sleeping person must come into close contact with the conductive fiber.

[3] The method using oxygen saturation also inconveniences a sleeping person because sensors must be attached to the sleeping person's fingers, ears and the like.

[4] The method using the wrist/waist type actigraph and an accelerometer cannot completely eliminate the inconvenience to patients because the accelerometer must be mounted on the wrist or the waist.

Meanwhile, in the case where weak sleeping stages 1~2 do not proceed to strong sleeping stages 3~4 due to snoring, insomnia or the like, it may be difficult to enjoy normal life due to drowsiness experienced during the daytime in daily life. In order to analyze such sleeping stages, electroencephalogram analysis using polysomnography, which is conducted in a hospital, must be carried out.

In the electroencephalogram analysis, the sleeping person's brain waves measured during sleep are divided according to frequency range, and the sleeping stages are determined based on the intensities in respective frequency ranges.

However, electroencephalogram analysis is performed by attaching electrodes to the head of a patient, so that it is difficult for the patient to sleep as usual due to the unfamiliar electrodes.

Movement that occurs during sleep is an important factor indicating whether a sleeping person has awoken. When movement occurs during sleep, the sleeping person is in a slightly awoken state or a completely awoken state. Accordingly, whether the sleeping person sleeps or is awake by analyzing the movement can be detected.

For the measurement of movement, a wristwatch type or waist attachment type movement detection device using an accelerometer has been developed. However, the wrist type/waist type detection device is problematic in that it may disturb the sleep of the sleeping person because inconvenience during sleep must be endured.

Furthermore, most existing sleep measurement devices are disadvantageous in that they cannot provide various sleep analysis signals.

TECHNICAL PROBLEM

Accordingly, the present invention has been made keeping in mind the above problems occurring in the prior art, and an object of the present invention is to provide an apparatus for analyzing a sleep structure according to non-restrictive weight detection, which allows weight detection devices to be installed in equipment, such as a bed that can be slept in, and measures variation in weight that depends on the movement or tossing and turning of a sleeping person, thus measuring various information, such as movement during sleep, the intensity and duration of the movement, variation in location, variation in position, and heartbeat characteristics, in a non-restrictive manner, so that the more accurate analysis of sleeping patterns can be conducted.

TECHNICAL SOLUTION

In order to accomplish the above object, the present invention provides an apparatus for analyzing a sleep structure according to non-restrictive weight detection, the apparatus including a weight detection means installed in equipment, which can be slept in, and configured to detect a target person's weight in a non-restrictive manner; and a controller configured to detect information about the sleep of the target person by detecting variation in the target person's weight measured by the weight detection means when the target person sleeps, and analyze the sleeping pattern of the target person.

The equipment, which can be slept in, is a bed or a chair formed to enable sleep, the weight detection means is a load cell, and the load cell comprises one or more load cells.

In addition, the present invention further includes amplifiers for amplifying signals measured by the weight detection means; low-pass filters for outputting low-pass filtered signals that belong to signals amplified by the amplifiers; high-pass filters for outputting high-pass filtered signals that belong to the signals amplified by the amplifiers; and a multiplexer configured to select any one from among the outputs of the low-pass filters and the high-pass filters under control of the controller.

The controller detects the body weight value of the target person and the location of a center of gravity based on the outputs of the low-pass filters, and determines the extent of movement based on the location of the center of gravity, thus determining the sleeping pattern. Furthermore, the controller measures variation and intensity in the target person's movement and detects variation in position and heartbeat characteristics, based on the outputs of the high-pass filters, thus determining the sleeping pattern.

Furthermore, in order to accomplish the above object, the present invention provides an apparatus for analyzing sleeping patterns based on non-restrictive weight detection, the apparatus includes one or more weight detection sensors installed in equipment, which can be slept in, and configured to detect the weight of a target person in a non-restrictive manner; amplifiers for amplifying signals measured by the weight detection sensors; low-pass filters for outputting low-pass filtered signals that belong to signals amplified by the amplifiers; high-pass filters for outputting high-pass filtered signals that belong to the signals amplified by the amplifiers; a multiplexer for selecting any one from among the outputs of the low-pass filters and the high-pass filters; a controller configured to detect information about the target person's sleep from the low-pass filtered signals and the high-pass filtered signals, which belong to the outputs of the high-pass filters and the low-pass filters, respectively, and are input through the multiplexer, and determine the target person's sleeping pattern; and a display unit for displaying the determination results of the controller.

The sleep information detected based on the low-pass filtered signal is information about the extent of the target person's movement based on the value of body weight of the target person and the location of the center of gravity, and the sleep information detected based on the high-pass signal is information about variation and the intensity of the target person' movement, variation in position, and heartbeat characteristics.

ADVANTAGEOUS EFFECTS

The apparatus for analyzing a sleep structure according to non-restrictive weight detection according to the present invention has the following effects:

First, the present invention can be utilized for a preliminary examination for finding out whether it is necessary to more intensively analyze sleeping stages using polysomnography. That is, in order to measure the influence of napping, insomnia, snoring, etc. upon sleep, polysomnography is carried out in a hospital after a plurality of electrodes and sensors have been attached to a sleeping person. Such polysomnography inconveniences the sleeping person due to the use of many electrodes and sensors, and incurs considerable expense. Furthermore, since the sleeping person must spend a day in the polysomnography room of the hospital, a lot of time is wasted. The present invention can be used for a preliminary examination for finding out whether it is necessary to more intensively analyze sleeping stages using polysomnography and, therefore, expenses and time can be saved.

Second, the present invention measures the sleeping person's movement during sleep without attaching any type of sensors or electrodes when the sleeping person is in an unnoticeable state on a bed, so that it is very convenient. Furthermore, the present invention enables the precise measurement of the sleeping person's movement because it directly measures movement.

Third, the present invention can acquire low-pass filtered signals and high-pass filtered signal, thus acquiring various pieces of information about the body weight of a sleeping person, the distance moved during sleep, movement out of a patient's location on a bed and the time thereof, the intervals between movements and the extent of movement, the degree of heart muscle activity, the heartbeat using a ballistocardiogram, and variation in position during sleep.

DESCRIPTION OF DRAWINGS

FIG. 5 is a table showing the distance moved in the bed during sleep;

FIG. 9 is a table showing movement in each sleeping stage according to the present invention;

FIG. 13 is a table showing comparison results of a electrocardiogram and a ballistocardiogram.

DESCRIPTION OF REFERENCE NUMERALS OF PRINCIPLE ELEMENTS

1: bed
10a-10d: load cell
20a-20d: differential amplifiers
30a-30d: low-pass filter
30e-30h: high-pass filter
40: multiplexer
50: controller
60: display unit

MODE FOR INVENTION

Embodiments of the present invention are described in detail with reference to the accompanying drawings below. The following embodiments are only examples of the present invention and the details of the present invention are not limited to the following embodiments.

The present invention measures variation in weight depending on the tossing and turning or movement of a sleeping person by installing weight detection devices on equipment that can be slept in, and analyzes the sleeping person's sleeping pattern during sleep based on a measured weight variation signal. Although, in the present invention, the case where the weight detection devices are installed in a bed is described, the present invention is not limited to this.

Figure 1:
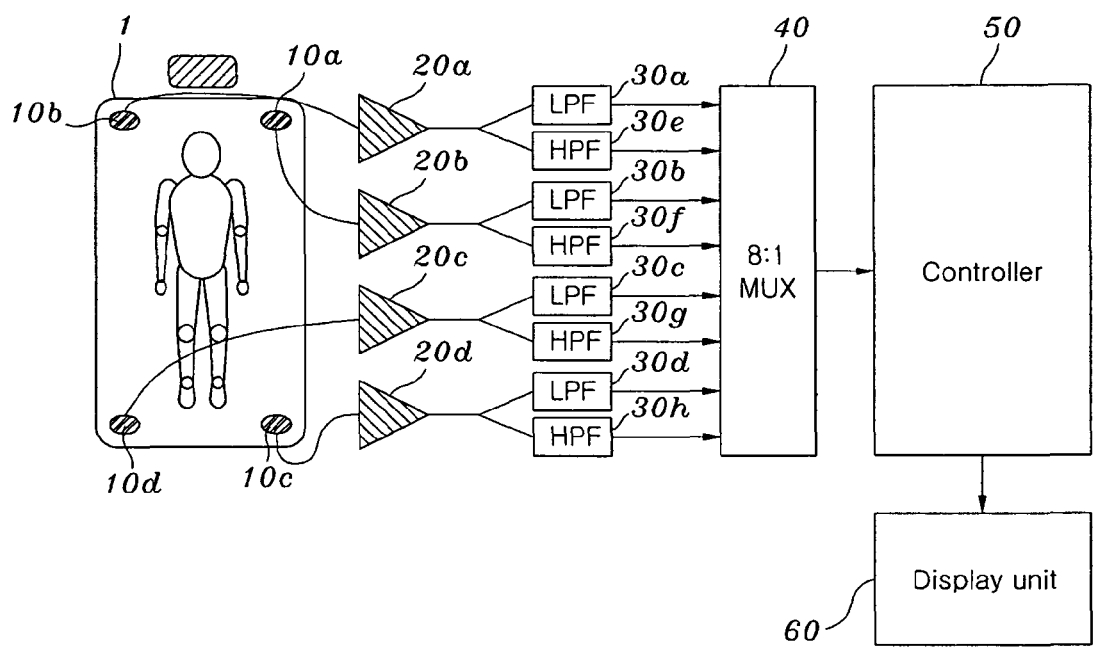
FIG. 1 is a diagram showing the construction of an apparatus for analyzing a sleep structure according to non-restrictive weight detection according to the present invention.

FIG. 1 is a diagram showing the construction of an apparatus for analyzing a sleep structure according to non-restrictive weight detection according to the present invention.

As shown in the drawing, the apparatus includes load cells 10a-10d installed on the four legs of a bed 1, and configured to detect the body weight of a sleeping person, differential amplifiers 20a-20d for amplifying signals measured by the load cells 10a-10d, Low-Pass Filters (LPFs) 30a-30d and High-Pass Filters (HPFs) for outputting low-pass filtered signals and high-pass filtered signals 30e-30h from the outputs of the differential amplifiers 20a-20d, respectively, a multiplexer (MUX) 40 for selecting any one from among the outputs of the LPFs 30a-30d and the HPFs 30e-30h, a controller 50 for analyzing the sleeping person's sleeping pattern based on the output of the multiplexer 40, and a display unit 60, such as a Liquid Crystal Display (LCD), for displaying results obtained from the analysis of the sleeping pattern by the controller 50.

The LPFs 30a-30d and the HPFs 30e-30h employ 2-pole Sallen-Key type secondary filters to perform low-pass filtering and high-pass filtering. Cut-off frequencies used to obtain low-pass and high-pass filtered signals are 20 Hz and 0.2 Hz, respectively.

The multiplexer 40 is an 8:1 multiplexer that selects one from among the output signals of the LPFs 30a-30d and the HPFs 30e-30h under the switching control of the controller 50.

The controller 50 performs an analog/digital conversion function of converting a signal acquired from the multiplexer 40 into a digital signal, and performs serial communication with devices, such as a computer or a notebook, thus outputting results obtained from the analysis of the sleeping pattern.

Furthermore, the controller 50 measures the weight of the sleeping person and variation in the center of gravity in the bed based on low-pass filtered signals, which are the outputs of the LPFs 30a-30d and are input through the multiplexer 40, and measures variation/intensity in the sleeping person's movement, variation in position, and mechanically transferred heart activity based on high-pass filtered signals, which are the outputs of the HPFs 30e-30h and are input through the multiplexer 40. Consequently, the controller 50 analyzes the sleeping pattern that indicates whether the sleeping person sleeps or is awake.

Although, in the present invention, the load cells 10a-10d, which are weight detection devices, are installed on the four legs of the bed 1, one or more load cells may be installed at predetermined locations on the base of the bed 1, in which case each load cell is provided with a LPF and a HPF. In the case where the number of load cells installed in the bed 1 is two, a 4:1 multiplexer is necessary. In the case where the number of load cells installed in the bed 1 is three, a 6:1 multiplexer is necessary. In the case where the number of load cells installed in the bed 1 is five, a 10:1 multiplexer is used.

In the present invention, constructed as described above, the signals of the respective load cells 10a-10d installed in the bed 1 are amplified through the differential amplifiers 20a-20d and are then filtered by the LPFs 30a-30d and the HPFs 30e-30h, and one of the filtered signals is input to the controller 50 through the multiplexer 40.

Figure 2:
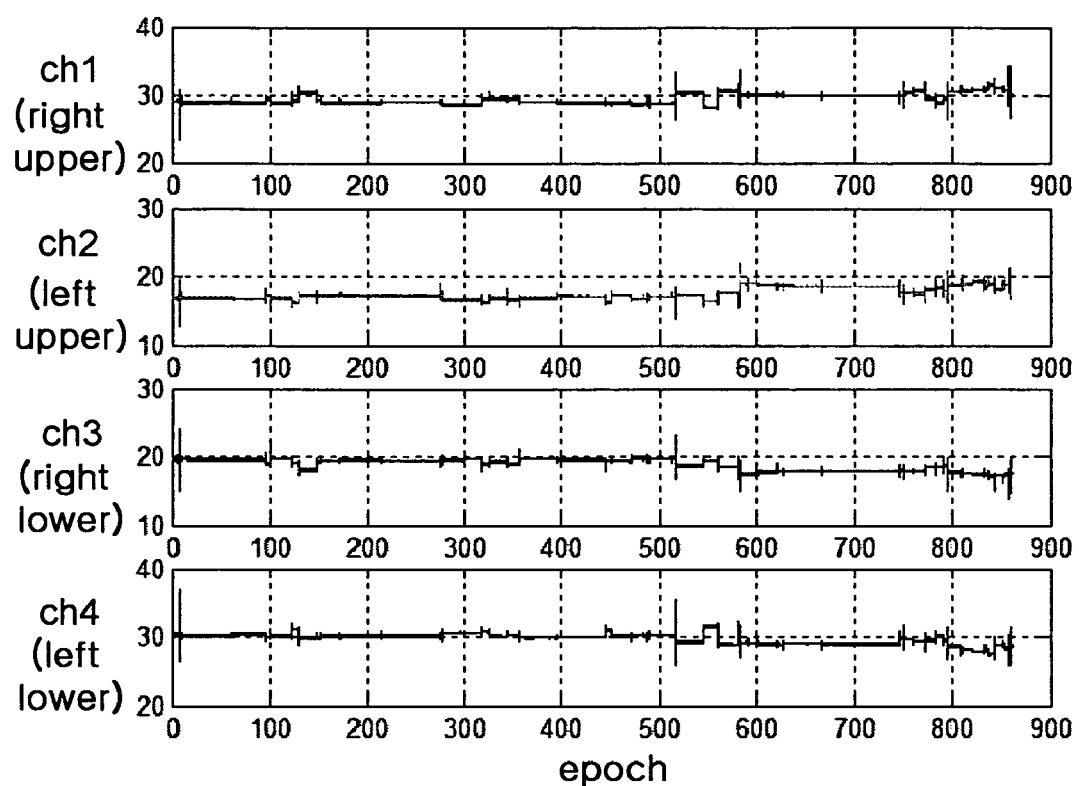
FIG. 2 is graphs showing signals measured using the low-pass filters and multiplexer of FIG. 1.

FIG. 2 is graphs showing an example of signals that are measured by the load cells 10a-10d and the LPFs 30a-30d when the sleeping person sleeps, and are input to the controller 50, and illustrates low-pass filtered signals Ch1-Ch4 acquired by right upper side, left upper side, right lower side and left lower side load cells 10a-10d in order from the upper side of FIG. 2 to the lower side thereof. In FIG. 2, variation in value with respect to time implies that a location has changed due to the movement of the sleeping person.

Figure 3:
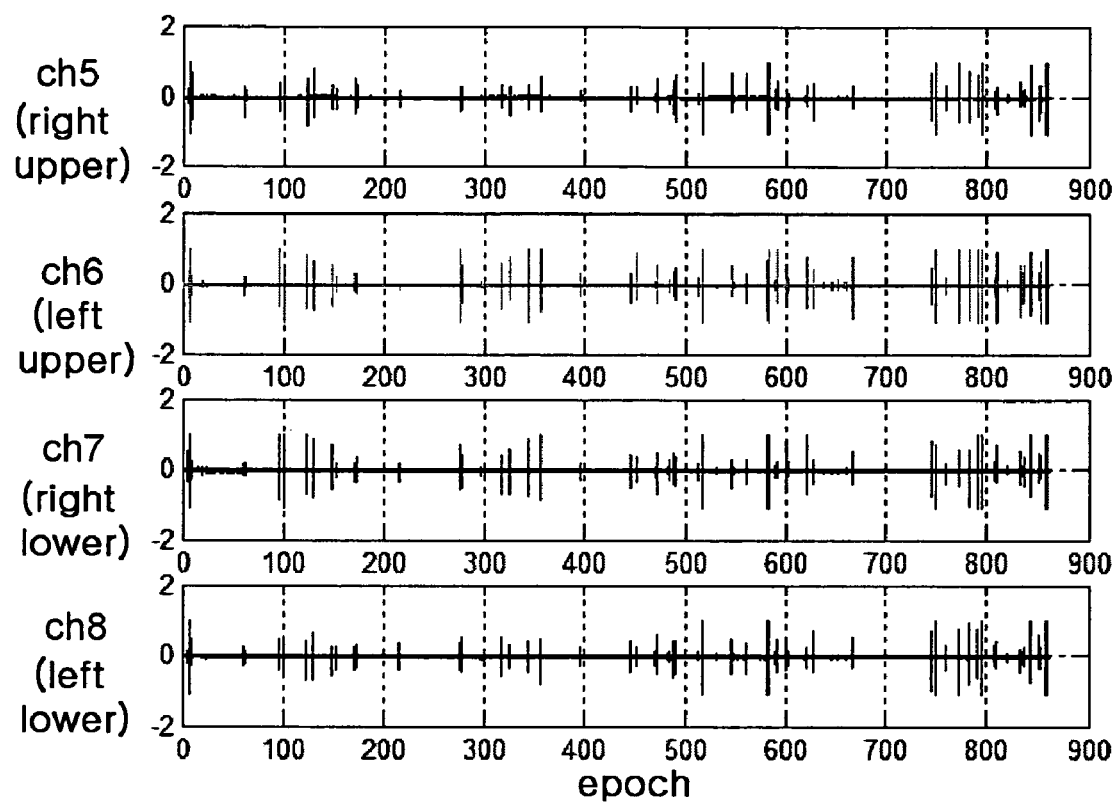
FIG. 3 is graphs showing signals measured using the high-pass filters and multiplexer of FIG. 1.

FIG. 3 is graphs showing an example of signals that are measured by the load cells 10a-10d the HPFs 30e-30h when the sleeping person sleeps and, and are input to the controller 50, and shows high-pass filtered signals Ch5-Ch8 acquired by right upper side, left upper side, right lower side and left lower side load cells 10a-10d in order from the upper side of FIG. 3 to the lower side thereof. In FIG. 3, fluctuation with respect to time implies that the sleeping person has moved in the bed 1.

The controller 50 analyzes the sleeping pattern, such as sleep/wakefulness, by analyzing the low-pass filtered signals, which are input through the LPFs 30a-30d, and the high-pass filtered signals, which are input through the HPFs 30e-30h, that belong to input signals, and displays the analysis results on the display unit 60.

First, analysis using the low-pass filtered signals is described below.

The low-pass filtered signals, which are measured by the load cells 10a-10d and are input to the controller 50 through the LPFs 30a-30d, are acquired to measure the center of gravity and variation in the center of gravity of the sleeping person on the bed 1, and the output signals of the load cells 10a-10d indicate weight values.

When the weight values are used, the weight of the sleeping person existing on the bed 1 can be detected. For example, if the weight values of the load cells 10a-10d are added up when a sleeping person having a weight of 60 Kg is sleeping in the bed 1, the actual weight of the sleeping person can be determined.

Furthermore, the measurement of time in and out of bed is one of the important observations to be made during sleep, and the time in and out of bed can be determined using the sum of the low-pass filtered signals of the output signals of the load cells 10a-10d.

That is, if the sleeping person does not move out of the bed 1, a constant body weight value is maintained throughout a total sleep period. In contrast, when the sleeping person moves out of the bed 1 during sleep, the weight has a value of "0" during the time out of bed. Consequently, information about a patient's behavior during sleep can be acquired.

Thereafter, the location of the sleeping person in the bed 1 can be determined using the low-pass filtered signals of the LPFs 30a-30d, and information about the sleeping person's movement during sleep using variation in the center of gravity sleeping person can be known.

Figure 4:
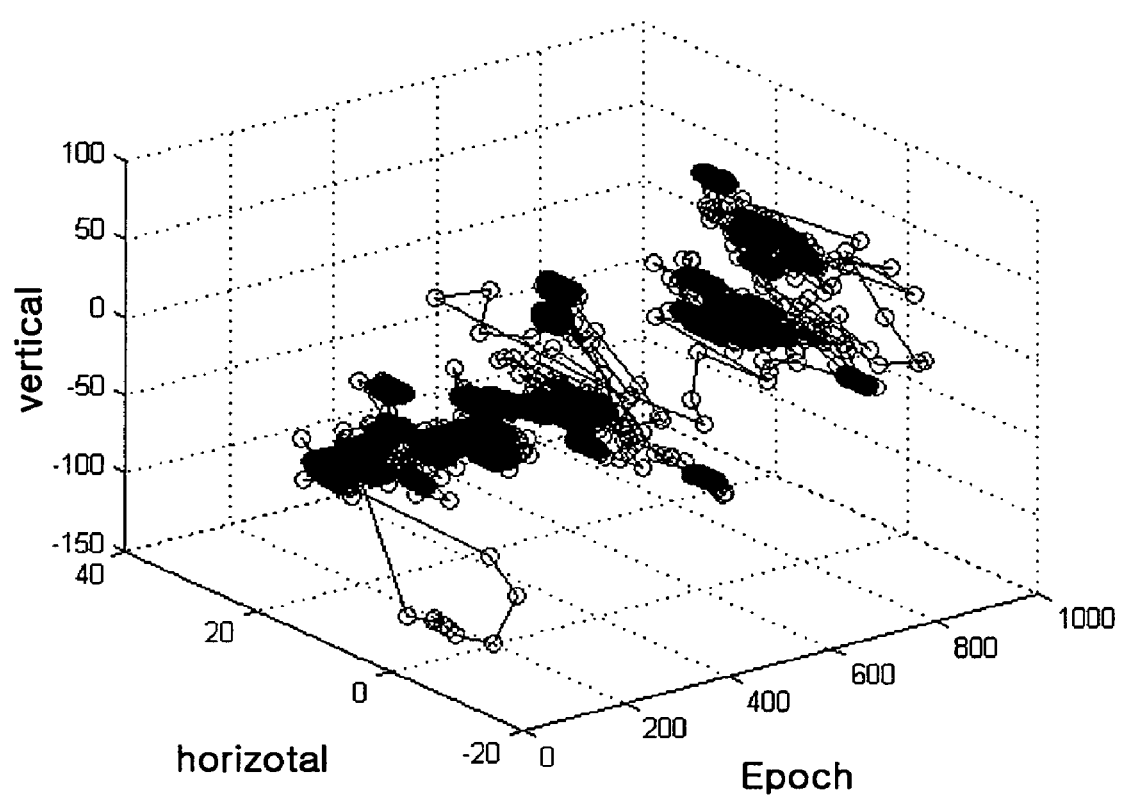
FIG. 4 is a diagram showing variation in the center of gravity on a bed during sleep.

The center of gravity is defined such that the center point of the bed 1 is a "0" point. FIG. 4 shows variation in the center of gravity in the bed 1 with respect to time. In FIG. 4, it can be seen that movement along a longitudinal axis is larger than movement along traverse axis.

Furthermore, the total distance moved on the bed 1 during sleep can be determined based on variation in location in the bed with respect to time.

The table of FIG. 5 shows the total distance moved obtained using the low-pass filtered signals and the distance moved, from which vibration caused by heart activity has been excluded. The value of variation in the center of gravity obtained when movement exists is a result obtained only during a period when movement exists.

In the table of FIG. 5, it can be seen that the value of variation in the center of gravity during sleep is considerably high. The reason why the value of variation is high is that effects occur as if the respective load cells 10a-10d were affected by movement in the bed 1 generated both by heartbeat and by variation in the center of gravity occurs. In the table of FIG. 5, it can be seen that the value of variation in the center of gravity for each unit of time, which is obtained when there is movement, is slightly high in contrast to the value of variation for a total time period.

Analysis using the high-pass filtered signals is described below.

The high-pass filtered signals are acquired to measure the variation and intensity in movement of the sleeping person in the bed 1 during sleep 1, the mechanically transferred heart activity, and variation in position.

In order to detect slight variation in weight caused by minute movements, the DC offsets of the high-pass filtered signals are removed using the HPFs 30e-30d. The high-pass filtered signals have a frequency range of 0.2 Hz to 10 Hz.

In order to detect movement during sleep, the intensity of movement is detected using the high-pass filtered signals, which are some of the acquired signals and, therefore, the duration, intensity and peak value of the movement can be analyzed.

In order to obtain the intensity of movement, the output values ($W_i$) of the HPFs 30e-30h are squared, and the sum of the outputs of the HPFs 30e-30h is calculated. The square root of the sum is extracted and, thereby, the following Equation 1 is obtained.

$$I(n) = \sqrt{\sum_{i=5}^{i=8} (W_i(n))^2} \quad (1)$$

The reference value (Xr) for movement is defined as a value for a predetermined time period (for example, 3 seconds) for which the smallest moved intensity is represented at 10 epochs after recording is started. In the case where the intensity of movement for the predetermined time period (time identical to the time for measuring the reference value) is two times larger then the reference value after the reference value has been obtained, it is determined that movement has occurred.

Figure 6:
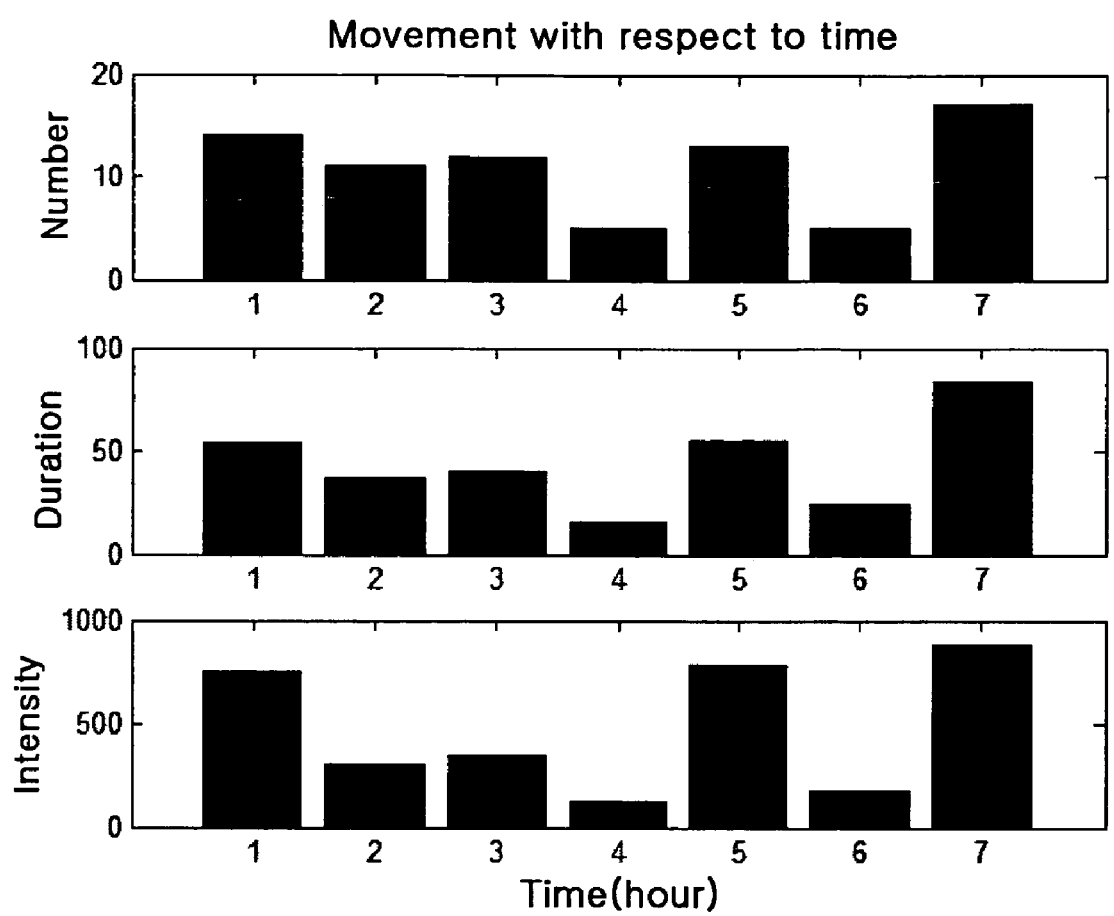
FIG. 6 is a diagram showing the number of movements with respect to time, the duration of the movements for with respect to time, and the intensity of the movements with respect to time through the analysis of a high-band signal according to the present invention.

FIG. 6 shows the number of movements, the duration of the movements, and the intensity of the movements with respect to time.

Figure 7:
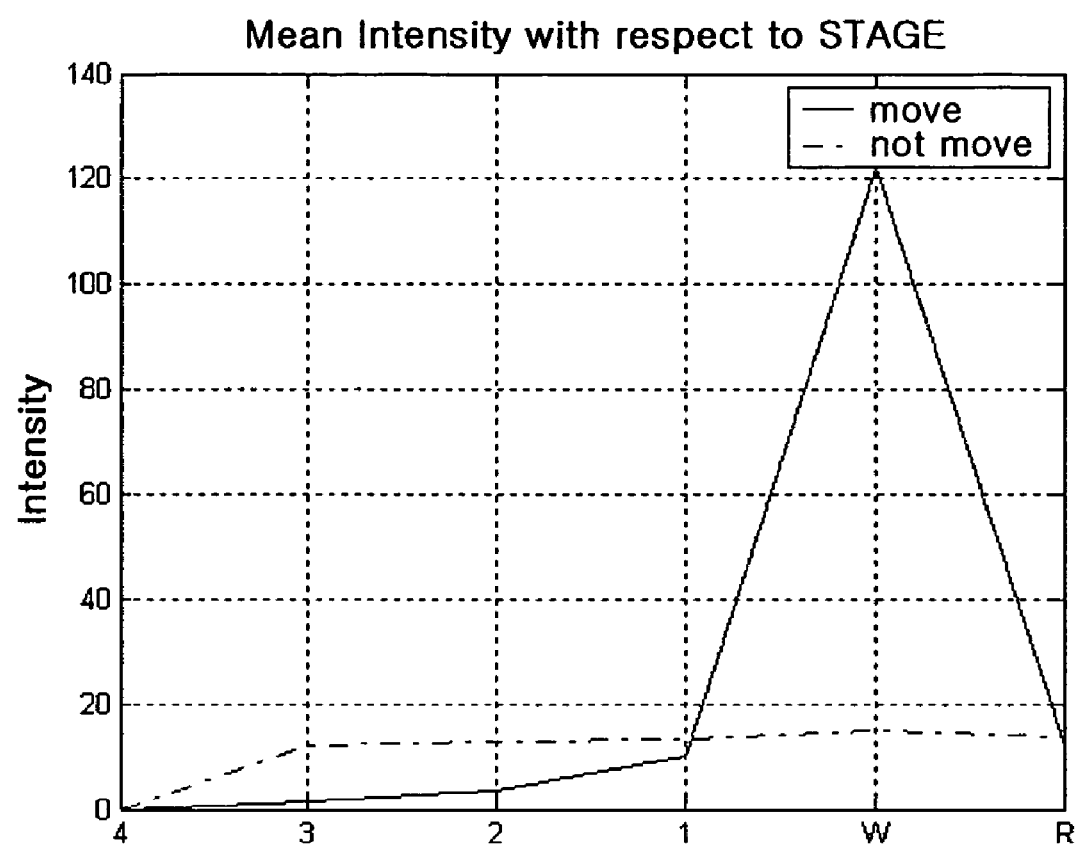
FIGS. 7 and 8 are diagrams showing characteristics of intensity and duration for each sleeping stage according to the present invention.
Figure 8:
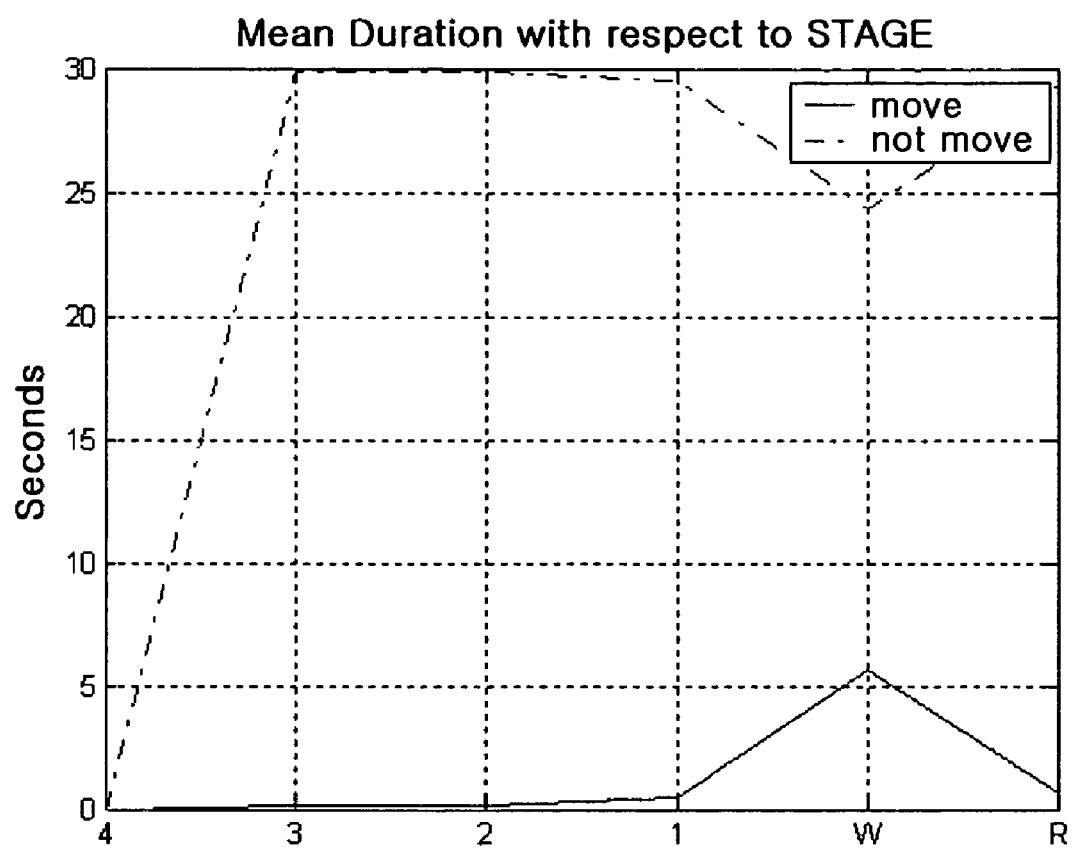

When movement during sleep is analyzed according to sleep stages that are distinguished using polysomnography, the graphs of FIGS. 7 and 8 can be acquired. In the graphs, the epoch of each unit of 30 sec is divided into intervals at which movement occurred and intervals at which movement did not occur, and the intensity/duration of movement are obtained. It can be seen that the greatest intensity/duration of movement occur during the stages of wakefulness, and the least intensity/duration occur during deep sleeping stages (stages 3 and 4).

Furthermore, it can be seen that movement characteristics during stage 1 and movement characteristics during a REM sleep stage are very similar to each other. In the table of FIG. 9, it can be seen that the results of FIG. 9 are similar to the results represented in the study of Wolpert. In FIG. 9, the fourth one of the sleeping stages of a target person does not appear at the time of experimentation and, therefore, there is no information about the fourth stage.

Analysis using a ballistocardiogram and a movement intensity signal is described below.

Information about the activity of heart muscle can be obtained using an electrocardiogram (ECG). Similarly, effects resulting from the activity of heart muscle can be measured when the acceleration of blood is directly measured based on a ballistocardiogram. The present invention can measure the same movement as can a ballistocardiogram.

That is, the fluctuation of a signal depending on the activity of a patient's heart is observed from the high-pass filtered signals having passed through the HPFs 30e-30h in a state in which the patient does not move.

Figure 10:
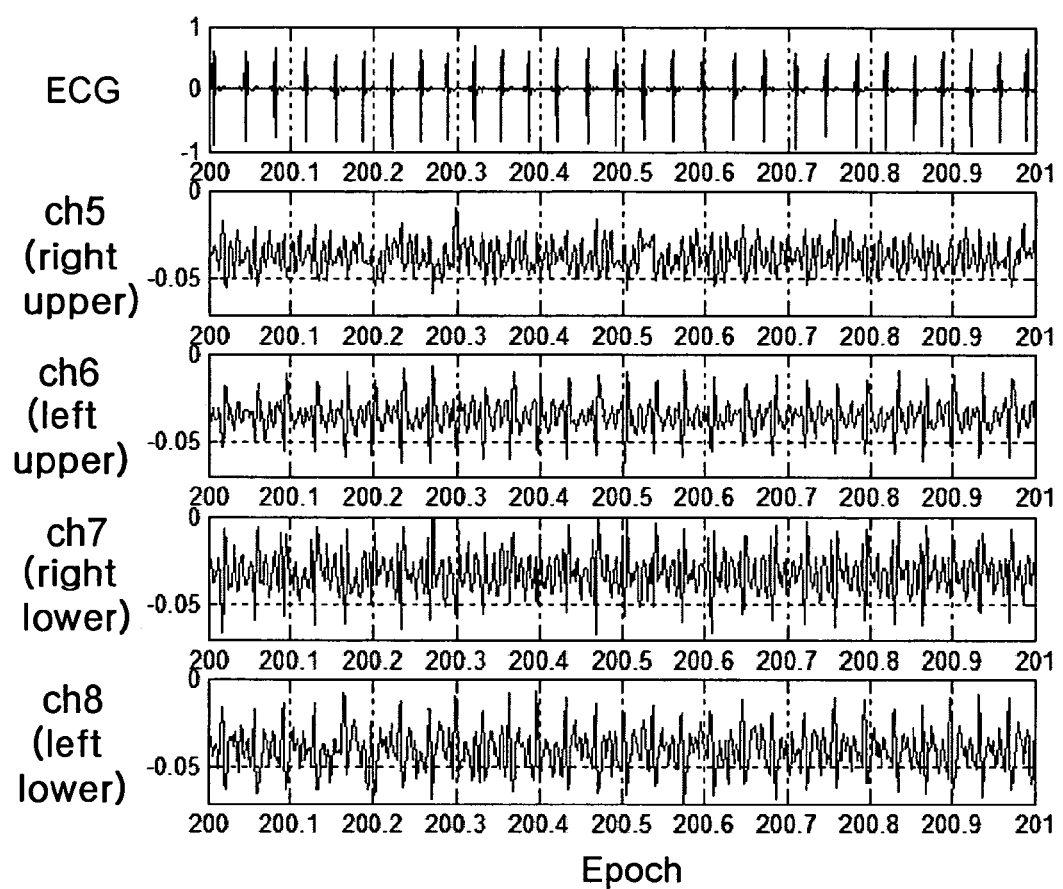
FIG. 10 is a diagram showing both an electrocardiogram and the results obtained by measuring the output signals of load cells according to the present invention.

FIG. 10 shows results simultaneously obtained by measuring vibration of the bed 1 and from an ECG. In FIG. 10, it can be seen that the outputs of the load cells 10a-10d vary at intervals identical to those of the QRS wave of the ECG.

Figure 11:
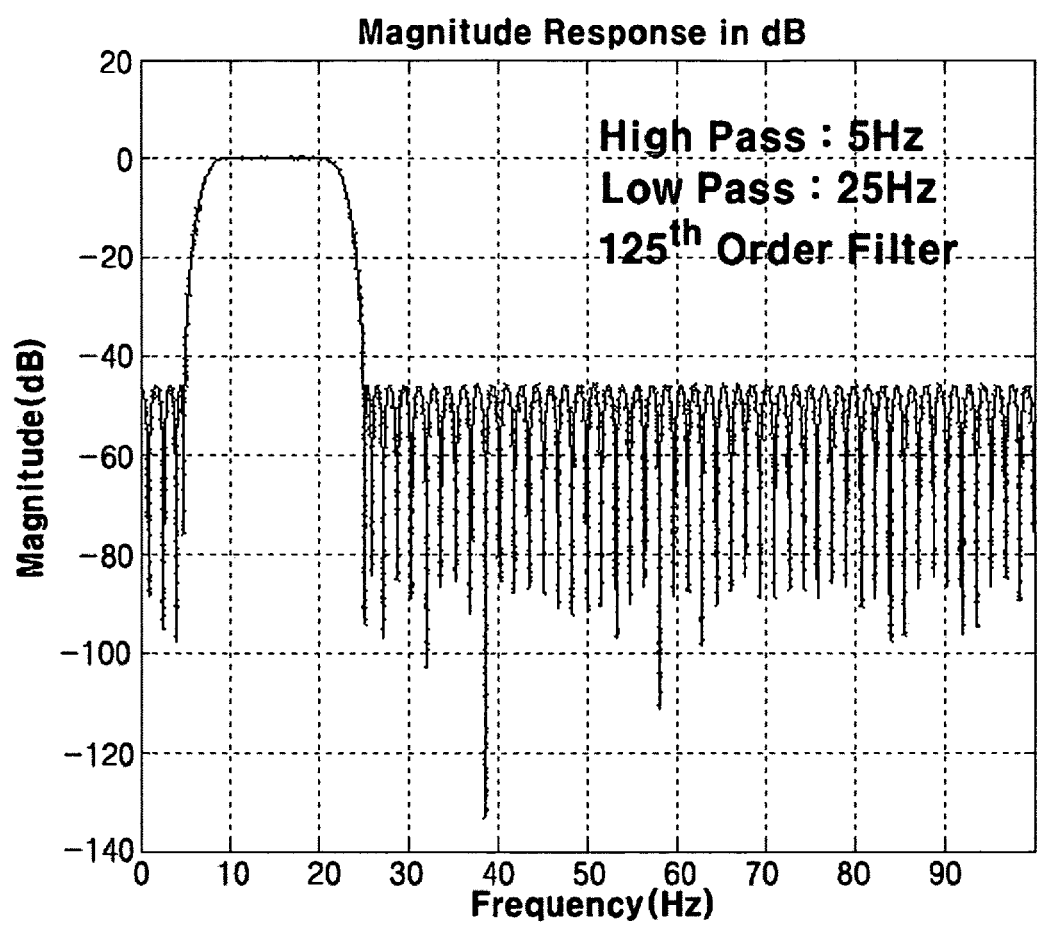
FIGS. 11 and 12 are diagrams showing the characteristics of low-pass filters and high-pass filters used in the ballistocardiogram of the present invention, and the results of filtering using the filters.
Figure 12:
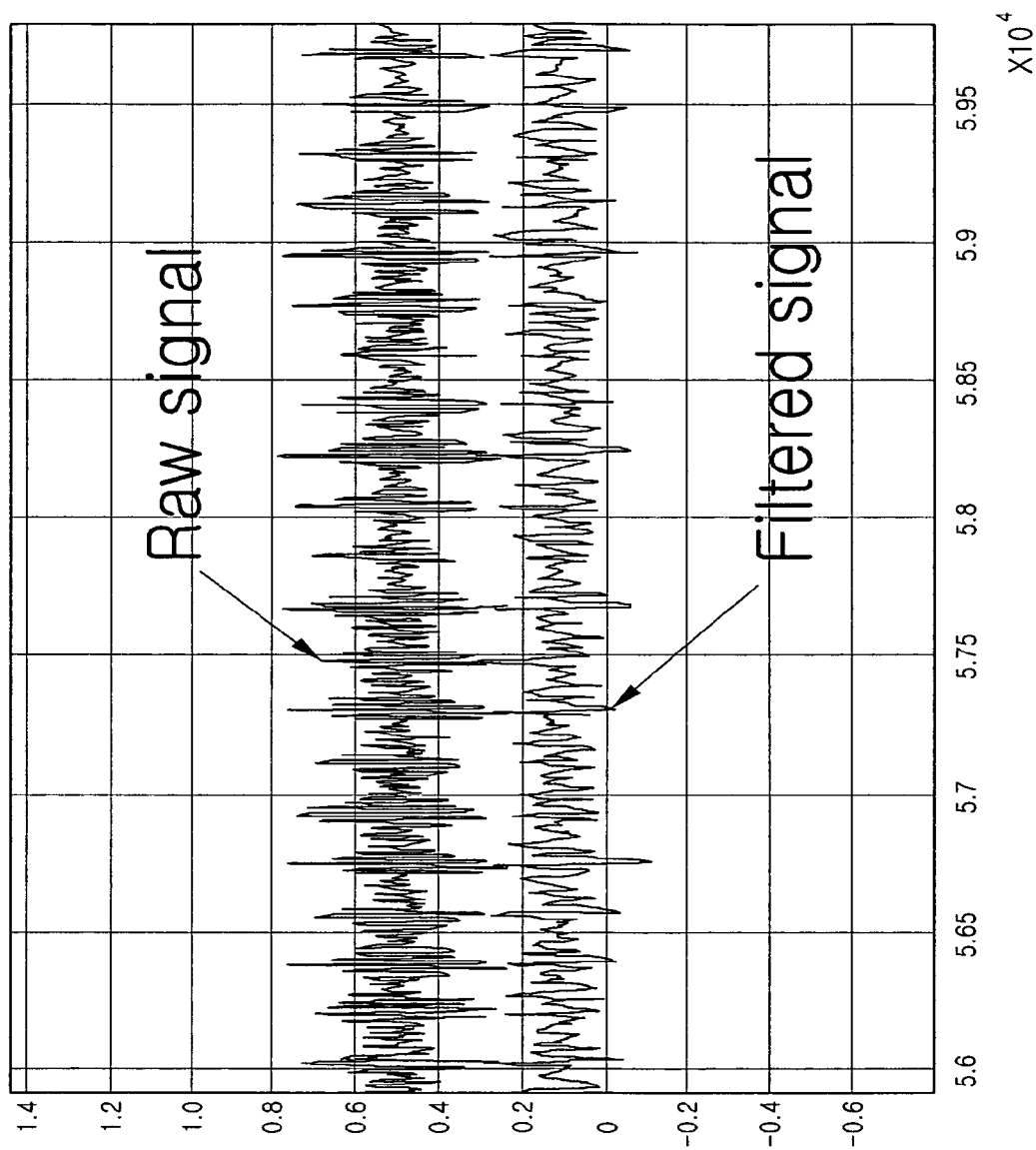

If the LPFs 30a-30d, having a cutoff frequency of 5 Hz, and the HPFs 30e-30h, having a cutoff frequency of 20 Hz, are employed for the acquired signals (FIG. 11) in order to measure heartbeat using the outputs of the load cells 10a-10d, the filtering result is represented as FIG. 12.

In this case, for the purpose of convenience, the vibration of a bed due to heart activity is defined as a Ballistocardiogram (BCG). In order to measure heartbeat based on the output signals of load cells 10a-10d, a Multiplication Of Backward Difference (MOBD) method is used (Suppappola, S., and Sun, Y., Nonlinear Transforms of ECG Signals for Digital QRS Detection: A Quantitative Analysis. IEEE Tran. Biomed. Eng., 1994. 41(4): p. 397-400.).

In the MOBD, a primary backward difference is used. when x[n] is defined as a primary backward difference in an nth sample, x[n] is obtained as follows:

$$x[n]=u[n]-u[n-1] \quad (2)$$

where, u[n] denotes filtered data. MOBD having an N order of magnitude is defined as follows:

$$y[n] = \prod_{k=0}^{N-1} |x[n-k]| \quad (3)$$

where, if all the signs of N backward difference values does not coincide in order to guarantee sign coherence, the resulting value y[n] is set to "0".

$$y[n]=0, \text{ if sgn}(x[n-k]) \neq \text{sgn}(x[n-(k+1)]),$$

$$k=0,1,\hat{},N-2 \quad (4)$$

where the sgn function designates a signum function returning a value of 0 or ±1 after the sign of the value of the sample.

Generally, in the maximum value, continuous increase is represented. Accordingly, when the sign coherence is guaranteed, a candidate with respect to an interval that represents the highest value of signal components may be determined. High frequency noise signals caused by environmental noise can be eliminated.

When correction is carried out for the time interval, among intervals in which the sign coherence is represented, the highest value during each heartbeat period can be obtained. The table of FIG. 13 indicates the characteristics of the electrocardiogram and the ballistocardiogram.

The results are described. It can be seen that a uniform time delay (0.4 sec) exists between the electrocardiogram and the ballistocardiogram. Furthermore, it can be seen that the coincidence of the highest peak of the ballistocardiogram with the highest peak of the electrocardiogram that can be obtained in an interval in which there is no movement is about 94%.

That is, it can be seen that, although an average time of about 0.4 seconds is taken to transfer a pulse wave generated by the electrocardiogram measurement to the load cells 10a-10d and, therefore, a delay occurs at the time of the transfer of the pulse wave, the characteristics of the pulse wave are not changed. Consequently, it can be seen that heartbeat characteristics can be detected by the load cells 10a-10d.

In FIG. 13, n(ECG): the number of peaks obtained from an ECG signal peak, n(BCG): the number of peaks obtained from a BCG signal, n(ECGnon): the number of ECG peaks obtained when intervals in which there is movement are excluded, n(BCGconsistent): the number of ECG peaks based on an ECG in intervals in which there is no movement, and tdelay: a time delay (seconds) taken to transfer the peak of the ECG peak to the load cells.

Thereafter, the detection of variation in position during sleep using frequency characteristics based on the high-pass filtered signals is described below.

The variation in position during sleep provides information related to apnea symptoms during sleep. Generally, in the case of a patient whose apnea symptoms are not serious, the apnea symptoms can be considerably alleviated when a lateral position is assumed.

In polysomnography, the variation in the patient's position is measured by attaching a body position sensor to his or her shoulder or the like to find his or her position during sleep. However, in the present invention, the position during sleep can be detected based on the outputs of the HPFs 30e-30h.

In the bed, the area in which bedsprings are pressed and the degree of deformation of the bed springs varies with the patient's position. The resonance characteristics of the springs vary according to the area in which bedsprings are pressed and the degree of deformation of the bedsprings varying with the patient's position, and the variation in position of the patient can be detected using the resonance characteristics.

Figure 14:
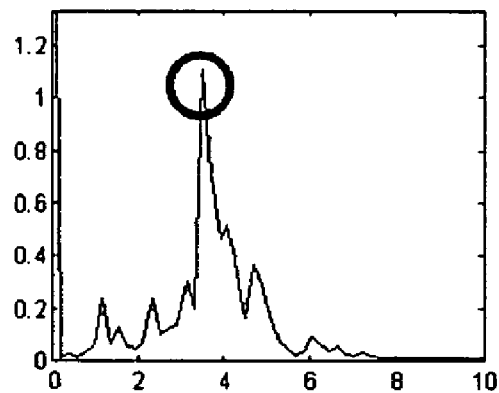
FIGS. 14 to 16 are diagrams showing the frequency characteristics of load cells with respect to position according to the present invention.
Figure 14:
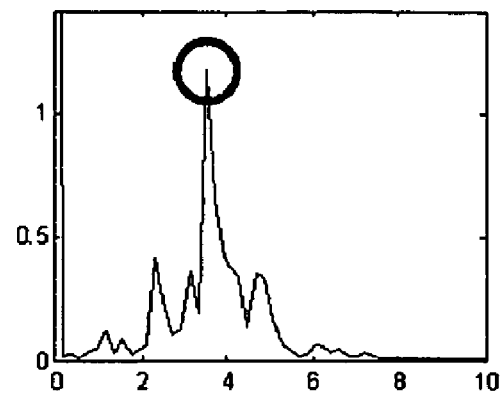
Figure 14:
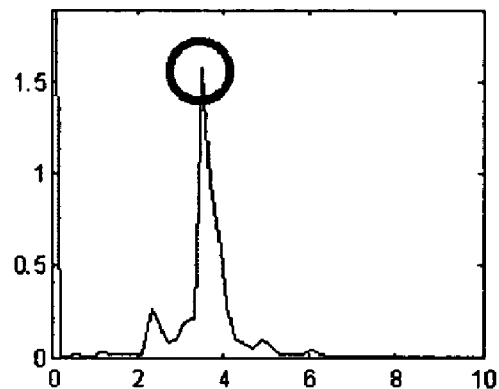
Figure 14:
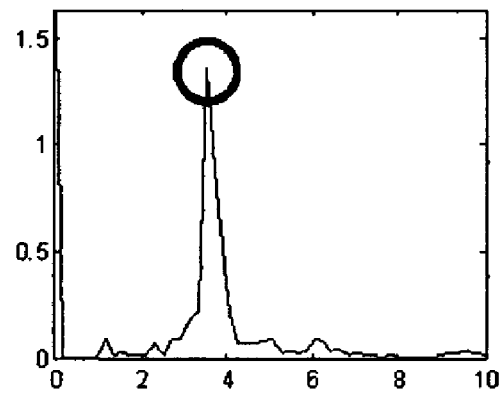
Figure 15:
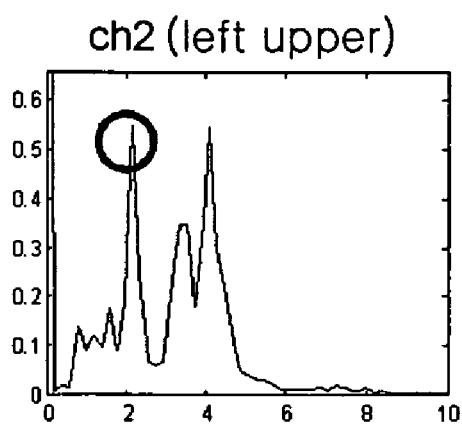
Figure 15:
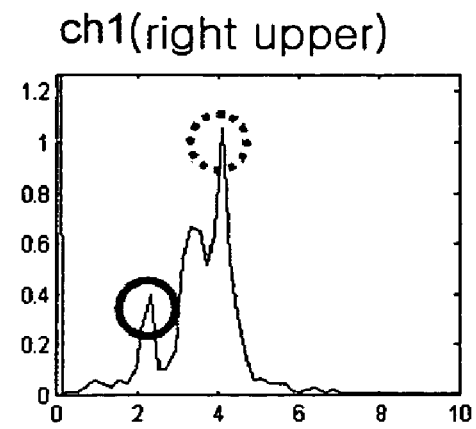
Figure 15:
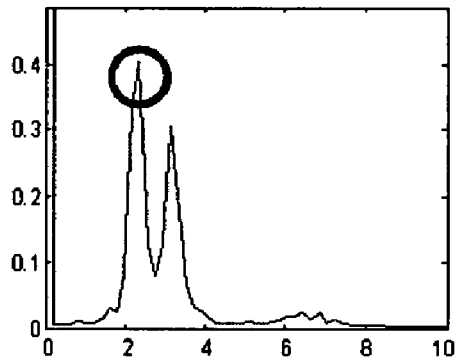
Figure 15:
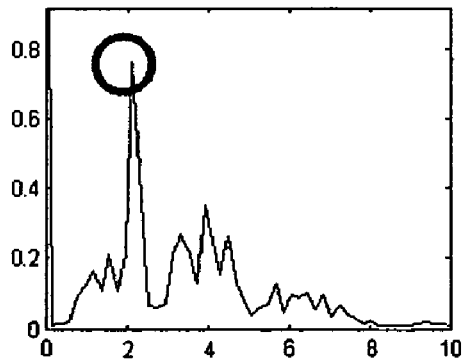
Figure 16:
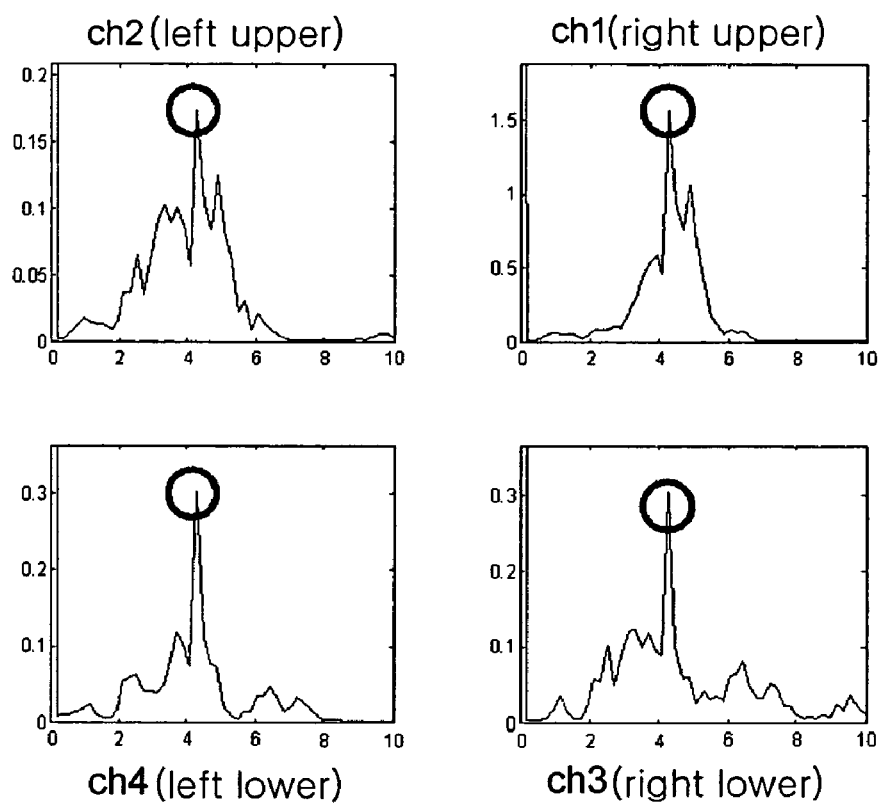

FIGS. 14 to 16 are diagrams showing frequency characteristics depending on the variation in position. In FIG. 14, it can be seen that the frequency having the highest peak in frequency analysis varies according to whether a supine position, a lateral position, or a prone position is assumed. Furthermore, it can be seen that the highest value is obtained at the highest frequency in the prone position, and the highest value is obtained at the lowest frequency in the lateral position.

In FIGS. 14 to 16, Ch1 indicates the frequency characteristic of the load cell 10a located at the right upper side of the bed 1, Ch2 indicates the frequency characteristics of the load cell 10b located at the left upper side of the bed 1, Ch3 indicates the frequency characteristics of the load cell 10c located at the right lower side of the bed 1, and Ch4 indicates the frequency characteristics of the load cell 10d located at the left lower side of the bed 1. In FIG. 14, the frequency having the highest value is 3.6~3.8 Hz. In FIG. 15, the frequency having the highest value is 2~2.2 Hz. In FIG. 16, the frequency having the highest value is 4~4.2 Hz.

As described above, the present invention analyzes the sleeping person's sleeping pattern in such a manner as to detect instantaneous and continuous variation in weight depending on the movement or tossing and turning of the sleeping person using devices for measuring variation in weight depending on tossing and turning, and movement, and detecting the sleeping pattern, that is, sleeping stages during sleep, as load cells 10a-10d installed on the legs of the bed 1, and to analyze the results at the controller 50.

The controller 50 determines the sleeping person's weight and variation in the center of gravity on the bed based on the low-pass filtered signals that are the outputs of the LPFs 30a-30d, and determines the variation and intensity in movement of the sleeping person, the variation in position, and heartbeat characteristics based on the high-pass filtered signals that are the outputs of the HPFs 30e-30h.

Furthermore, the controller 50 can more exactly analyze the sleeping person's sleeping pattern, that is, sleeping stages such as the sleeping person's wakefulness/sleep during sleep, through the determination, such as the measurement of the sleeping person's weight, variation in the center of gravity in the bed, the variation and intensity in movement of the sleeping person, the variation in position, and heartbeat characteristics based on the low-pass filtered signals and the high-pass filtered signals.

The embodiments of the present invention are not limited only to beds, but may be applied to couches, beds for outpatient health care at home, chairs and the like.

Although descriptions are made with reference to the embodiments of the present invention described above, it is appreciated to those skilled in the art that modification and variation may be made within the range without departing from the spirit and scope described in the following claims.

The invention claimed is:

1. An apparatus for analyzing a sleep structure according to non-restrictive weight detection, the apparatus comprising:
   first through fourth or more weight detection means installed respectively on the four legs of an equipment, which can be slept in, and configured to detect a target person's weight in a non-restrictive manner;
   a controller configured to detect information about sleep of the target person by detecting variation in the target person's weight measured by the weight detection means when the target person sleeps, and analyze a sleeping pattern of the target person and a sleeping pattern that indicates whether the sleeping person sleeps or is awake;
   first through fourth amplifiers for amplifying respectively signals measured by the first through fourth weight detection means;
   first through fourth low-pass filters for outputting low-pass filtered signals that belong to signals amplified by the first through fourth amplifiers;
   first through fourth high-pass filters for outputting high-pass filtered signals that belong to the signals amplified by the first through fourth amplifiers; and
   a multiplexer configured to select any one from among the outputs of the first through fourth low-pass filters and the first through fourth high-pass filters under control of the controller,
   wherein the controller detects a body weight value of the target person and a location of a center of gravity based on outputs of the first through fourth low-pass filters, and determines an extent of movement based on the location of the center of gravity, thus determining the sleeping pattern,
   wherein the controller measures variation and intensity in the target person's movement and detects variation in position and heartbeat characteristics, based on outputs of the first through fourth high-pass filters, thus determining the sleeping pattern,
   wherein the first through fourth amplifiers are respectively provided with the first through fourth low-pass filters and the first through fourth high-pass filters,
   wherein the multiplexer is a 8-bit multiplexer,
   wherein the controller measures the intensity by equation that the output values of the first through fourth high-pass filters are squared, the sum of the outputs of the first through fourth high-pass filters is calculated and the square root of the sum is extracted,
   wherein the controller measures the variation in the target person's movement by comparison between predetermined reference value and the intensity measured, for the predetermined time period.

2. The apparatus according to claim 1, wherein the equipment, which can be slept in, is a bed or a chair formed to enable sleep.

3. The apparatus according to claim 1, wherein the weight detection means is a load cell.

4. The apparatus according to claim 3, wherein the load cell comprises one or more load cells.

5. The apparatus according to claim 1, wherein the low-pass filters and the high-pass filters are 2-pole Sallen-Key type secondary filters.

6. The apparatus according to claim 1, wherein the controller is configured such that serial communication can be performed.

7. The apparatus according to claim 1, further comprising display means for displaying sleeping pattern determination results of the controller.

8. An apparatus for analyzing a sleep structure according to non-restrictive weight detection, the apparatus comprising:
first through fourth or more weight detection sensors installed respectively on the four legs of an equipment, which can be slept in, and configured to detect a weight of a target person in a non-restrictive manner;
first through fourth amplifiers for amplifying respectively signals measured by the first through fourth weight detection sensors;
first through fourth low-pass filters for outputting low-pass filtered signals that belong to signals amplified by the first through fourth amplifiers;
first through fourth high-pass filters for outputting high-pass filtered signals that belong to the signals amplified by the first through fourth amplifiers;
a multiplexer for selecting any one from among the outputs of the first through fourth low-pass filters and the first through fourth high-pass filters;
a controller configured to detect information about the target person's sleep from the low-pass filtered signals and the high-pass filtered signals, which belong to outputs of the first through fourth high-pass filters and the first through fourth low-pass filters, respectively, and are input through the multiplexer, and determine the target person's sleeping pattern,
wherein, sleeping pattern is formed of the target person's sleeping stages such as wakefulness/sleep; and
a display unit for displaying determination results of the controller,
wherein the sleep information detected based on the low-pass filtered signal is information about an extent of the target person's movement based on a value of body weight of the target person and the location of the center of gravity,
wherein the sleep information detected based on the high-pass signal is information about variation and intensity of the target person's movement, variation in position, and heartbeat characteristics,
wherein the first through fourth amplifiers are respectively provided with the first through fourth low-pass filters and the first through fourth high-pass filters,
wherein the multiplexer is a 8-bit multiplexer,
wherein the controller measures the intensity by equation that the output values of the first through fourth high-pass filters are squared, the sum of the outputs of the first through fourth high-pass filters is calculated and the square root of the sum is extracted,
wherein the controller measures the variation in the target person's movement by comparison between predetermined reference value and the intensity measured, for the predetermined time period.

9. The apparatus according to claim 8, wherein
the equipment, which can slept in, is a bed or a chair formed to enable sleep.

10. The apparatus according to claim 8, wherein the weight detection sensors are load cells.

11. The apparatus according to claim 8, wherein each of the low-pass filters and each of the high-pass filters are 2-pole Sallen-Key type secondary filers.

* * * * *